(12) United States Patent
Liu et al.

(10) Patent No.: US 12,226,191 B2
(45) Date of Patent: Feb. 18, 2025

(54) METHOD AND ELECTRONIC DEVICE FOR DYNAMICALLY ACQUIRING MAXIMAL OXYGEN CONSUMPTION

(71) Applicant: Guangdong Coros Sports Technology Co., Ltd., Guangdong (CN)

(72) Inventors: Xin Liu, Guangdong (CN); Xuan Rao, Guangdong (CN); Yu Tang, Guangdong (CN); Muyi Huang, Guangdong (CN); Haotian Niu, Guangdong (CN)

(73) Assignee: Guangdong Coros Sports Technology Co., Ltd., Dongguan (CN)

( * ) Notice: Subject to any disclaimer, the term of this patent is extended or adjusted under 35 U.S.C. 154(b) by 1009 days.

(21) Appl. No.: 17/204,322

(22) Filed: Mar. 17, 2021

(65) Prior Publication Data

US 2021/0353188 A1    Nov. 18, 2021

(30) Foreign Application Priority Data

May 13, 2020    (CN) .......................... 202010405218.0

(51) Int. Cl.
| | |
|---|---|
| *A61B 5/0205* | (2006.01) |
| *A61B 5/00* | (2006.01) |
| *A61B 5/024* | (2006.01) |
| *A61B 5/11* | (2006.01) |
| *A63B 24/00* | (2006.01) |

(Continued)

(52) U.S. Cl.
CPC ............ *A61B 5/0205* (2013.01); *A61B 5/024* (2013.01); *A61B 5/1118* (2013.01); *A61B 5/4866* (2013.01); *A61B 5/7278* (2013.01); *A63B 24/0062* (2013.01); *G16H 10/00* (2018.01); *G16H 20/30* (2018.01); *G16H 50/30* (2018.01); *A63B 2024/0065* (2013.01); *A63B 2220/30* (2013.01)

(58) Field of Classification Search
None
See application file for complete search history.

(56) References Cited

U.S. PATENT DOCUMENTS

| | | | | |
|---|---|---|---|---|
| 4,367,752 A | * | 1/1983 | Jimenez | ............... A61B 5/7475 |
| | | | | 600/595 |
| 2004/0102931 A1 | * | 5/2004 | Ellis | ..................... A61B 5/0833 |
| | | | | 702/188 |

(Continued)

FOREIGN PATENT DOCUMENTS

CN    106295805 A    1/2017

*Primary Examiner* — Michael R Bloch
(74) *Attorney, Agent, or Firm* — ANOVA LAW GROUP, PLLC (57) ABSTRACT

A method for dynamically acquiring maximal oxygen consumption includes acquiring user's age, gender, weight, resting heart rate and maximum heart rate; detecting basic heart rate data comprising a plurality of exercise heart rates and basic speed data comprising a plurality of exercise speeds; calculating a characteristic heart rate and a characteristic speed based on the basic heart rate data and the basic speed data; and calculating the user's maximal oxygen consumption according to the user's age, gender, weight, resting heart rate and maximum heart rate, the characteristic heart rate and the characteristic speed. The maximal oxygen consumption for each exercise can be dynamically calculated and the result is accurate.

16 Claims, 3 Drawing Sheets

(51) Int. Cl.
*G16H 10/00* (2018.01)
*G16H 20/30* (2018.01)
*G16H 50/30* (2018.01)

(56) References Cited

U.S. PATENT DOCUMENTS

| | | | |
|---|---|---|---|
| 2014/0372097 A1* | 12/2014 | Karvonen | A61B 5/02438 |
| | | | 703/13 |
| 2016/0206248 A1* | 7/2016 | Sartor | A61B 5/681 |
| 2017/0120108 A1* | 5/2017 | Nakazawa | A61B 5/11 |
| 2017/0156641 A1* | 6/2017 | Nyberg | A61B 5/6833 |
| 2018/0055446 A1* | 3/2018 | Sato | A61B 5/02438 |
| 2018/0368737 A1* | 12/2018 | Bonomi | A61B 5/7264 |

* cited by examiner

METHOD AND ELECTRONIC DEVICE FOR DYNAMICALLY ACQUIRING MAXIMAL OXYGEN CONSUMPTION

RELATED APPLICATIONS

This application claims the benefit of priority to Chinese invention application No. 202010405218.0 filed on May 13, 2020, which is hereby incorporated by reference in its entirety.

FIELD OF THE INVENTION

The present invention relates to technical field of exercise parameter monitoring, in particular to a method and an electronic device for dynamically acquiring maximal oxygen consumption.

BACKGROUND OF THE INVENTION

Material metabolism and energy metabolism are the basis of the functional activities of various tissues and organs in the body, and athletic ability is the concentrated expression of various functional activities of the body. According to different energy modes, athletic ability can be divided into aerobic exercise and anaerobic exercise. The ability of aerobic energy supply is the basis, and the maximal oxygen consumption ($VO_2$max) is the most commonly used and most effective method for evaluating aerobic capacity and refers to the maximum intensity of exercise in the human body. When the body is unable to support the exercise, the amount of oxygen that can be taken in is an important reflection of the body's aerobic athletic ability index.

At present, there are generally two methods for determining the maximal oxygen consumption, namely the direct test method and the indirect test method. The direct test method requires the tester wearing a special instrument to run on a treadmill or ride a power bicycle and adjusts the speed level to make the tester exercise to exhaustion, meanwhile equips a special instrument to collect and analyze the tester's breath to determine the maximal oxygen consumption. The indirect test method is based on the relevance between the human body's oxygen consumption and the own power and the heart rate during exercise, so the tester's maximal oxygen consumption is estimated from the heart rate during exercise and the power completed during exercise. In addition, the maximal oxygen consumption can be obtained by tests such as Bruce method or a 12-minute run.

It is the most accurate to detect the maximal oxygen consumption by the direct test method. However, due to the restriction of the detection equipment, it cannot be carried by the user portably, which is inconvenient as the maximal oxygen consumption during each exercise of the user cannot be measured in real time. Additionally, the maximal oxygen consumption is affected by factors such as age, gender, genetic factors, training, environmental and body fat rate, etc., as a result, the maximal oxygen consumption calculated by the current method through a simple calculation formula generally has large errors, which leads to an inaccurate result.

Therefore, it is necessary to improve the existing method of obtaining the maximal oxygen consumption to improve the accuracy of the calculation.

SUMMARY OF THE INVENTION

One of the objectives of the present invention is to provide a method for dynamically obtaining maximal oxygen consumption in order to solve the above technical problems, so as to detect maximal oxygen consumption during exercise and accurately evaluate the current aerobic capacity level for a user.

Another objective of the present invention is to provide an electronic device for dynamically acquiring maximal oxygen consumption, so as to detect maxima oxygen consumption during exercise and accurately evaluate the current aerobic capacity level for a user.

One more objective of the present invention is to provide a readable storage medium for dynamically acquiring maximal oxygen consumption, so as to detect maximal oxygen consumption during exercise and accurately evaluate the current aerobic capacity level for a user.

To achieve the above objectives, the present invention provides a method for dynamically acquiring maximal oxygen consumption including acquiring a user's age, gender, weight, resting heart rate and maximum heart rate, detecting basic heart rate data including a plurality of exercise heart rates and basic speed data including a plurality of exercise speeds, calculating a characteristic heart rate and a characteristic speed based on the basic heart rate data and the basic speed data and calculating the user's maximal oxygen consumption according to tire user's age, gender, weight, resting heart rate and maximum heart rate, the characteristic heart rate and the characteristic speed.

In comparison with tire prior art, the method for dynamically acquiring maximal oxygen consumption of the present invention not only needs to collect static data such as the user's age, gender, weight, resting heart rale, and maximum heart rate, but also needs to collect dynamic data such as the user's current basic heart rate data during exercise and basic speed data of body movement, and the basic heart rate data and basic speed data in the characteristic time period selected from the user's current exercise time are processed by an average algorithm to obtain the characteristic heart rate and characteristic speed. Then, the age, gender, weight, resting heart rate, maximum heart rate, characteristic heart rate, and characteristic speed are substituted into a formula to obtain the user's maximal oxygen consumption during the current exercise. By this token, on one hand, the maximal oxygen consumption during each exercise can be dynamically calculated, thereby providing accurate reference data for the user to evaluate the current aerobic capacity level; on the other hand, by using the formula to calculate the maximal oxygen consumption in the present invention, both static data and dynamic data of the user are combined, to achieve a high-accurate detection result.

Preferably, the user's maximal oxygen consumption is calculated according to a first formula:

$$VO_2\text{max} = A + P1*S - P2*G + P3*V*\frac{P4}{B} - C*\frac{HR_{chara} - HR_{rest}}{HR_{max} - HR_{rest}} - \frac{2(a-26)}{5},$$

wherein A is a constant from 40 to 50, P1 is a constant from 7 to 8, S is a gender constant, male is equal to 1, and female is equal to 0; P2 is a constant from 0.1 to 0.2, G is the user's weight; P3 is a constant from 4 to 5, V is the characteristic speed. P4 is a constant from 3 to 4, B is a constant from 1 to 2; C is a constant from 15 to 20, $HR_{chara}$ is the characteristic heart rate, $HR_{rest}$ is the resting heart rate in a quiet state for the user, $HR_{max}$ is the maximum heart rate; and a is the user's age.

Preferably, the characteristic heart rate is calculated by averaging the basic heart rate data and die characteristic speed is calculated by averaging die basic speed data.

Preferably, calculating a characteristic heart rate and a characteristic speed based on the basic heart rate data and the basic speed data includes detecting first basic heart rate data and second basic heart rate data, detecting first basic speed data and second basic speed data, generating a first unit heart rate and a second unit heart rate by averaging the first basic heart rate and the second basic heart rate data respectively, generating a first unit speed and a second unit speed by averaging the first basic speed data and the second basic speed data respectively, and calculating the characteristic heart rate by averaging the first unit heart rate and the second unit heart rate and calculating the characteristic speed by averaging the first unit speed and the second unit speed.

Preferably, when the maximum heart rate is generated in real time according to the user's age, the maximum heart rate is calculated by following formula: $HR_{max}=208-0.7*a$.

Preferably, the basic heart rate data and the basic speed data are detected when the user's single continuous exercise exceeds a preset duration.

Preferably, the method further includes displaying a calculated maximal oxygen consumption by following steps:

when calculating the maximal oxygen consumption for N consecutive times, calculating a display value XN according to a second formula: $X_N=(VO_2max1+VO_2max2 \ldots VO_2maxN)/N$, wherein $N \geq 1$, $VO_2maxN$ indicates the maximal oxygen consumption calculated at the Nth time.

Preferably, the method further includes determining whether a current number of consecutive calculations of maximal oxygen consumption N exceeds a present value M, if not, calculating the display value according to the second formula; otherwise, continuously calculating a moving average Xy of subsequent maximal oxygen consumptions by using a moving average algorithm with a fixed calculation length M. and determining whether the moving average $X_y$ is greater than a current display value, if yes, updating the current display value with the moving average $X_y$.

Accordingly, the present invention provides an electronic device for dynamically acquiring maximal oxygen consumption, the electronic device includes a heart rate detection module, a speed detection module and one or more processors. The heart rate detection module is configured to detect basic heart rate data including a plurality of exercise heart rates, the speed detection module is configured to detect basic speed data including a plurality of exercise speeds, the one or more processor are configured to acquire a user's age, gender, weight, resting heart rate and maximum heart rate, calculate a characteristic heart rate and a characteristic speed based on the basic heart rate data and the basic speed data, and calculate the user's maximal oxygen consumption according to the user's age, gender, weight, resting heart rate and maximum heart rate, the characteristic heart rate and the characteristic speed.

Preferably, the one or more processors are further configured to calculate the user's maximal oxygen consumption according to a first formula:

$$VO_2max = A + P1*S - P2*G + P3*V*\frac{P4}{B} - C*\frac{HR_{chara}-HR_{rest}}{HR_{max}-HR_{rest}} - \frac{2(a-26)}{5},$$

wherein A is a constant from 40 to 50, P1 is a constant from 7 to 8, S is a gender constant, male is equal to 1, and female is equal to 0; P2 is a constant from 0.1 to 0.2, G is user's weight; P3 is a constant from 4 to 5, V is characteristic speed, P4 is a constant from 3 to 4, B is a constant from 1 to 2; C is a constant from 15 to 20, $HR_{chara}$ is characteristic heart rate, $HR_{rest}$ is resting heart rate in a quiet stale for user, $HR_{max}$ is maximum heart rate; and a is user's age.

Preferably, to calculate the characteristic heart rate and the characteristic speed, the one or more processors are further configured to calculate the characteristic heart rate by averaging the basic heart rate data and calculate the characteristic speed by averaging the basic speed data.

Preferably, to calculate the characteristic heart rate and the characteristic speed, the one or more processors are further configured to detect first basic heart rate data and second basic heart rate data, detect first basic speed data and second basic speed data, generate a first unit heart rate and a second unit heart rate by averaging the first basic heart rate and the second basic heart rate data respectively, generate a first unit speed and a second unit speed by averaging the first basic speed data and the second basic speed data respectively, calculate the characteristic heart rate by averaging the first unit heart rate and the second unit heart rate, and calculate the characteristic speed by averaging the first unit speed anti the second unit speed.

Preferably, when the maximum heart rate is generated in real time according to the user's age, the maximum heart rate is calculated by following formula: $HR_{max}=208-0.7*a$.

Preferably, the basic heart rate data and the basic speed data are detected when the user's single continuous exercise exceeds a preset duration.

Preferably, the one or more processors are further configured to calculate a display value based on following steps:

when calculating the maximal oxygen consumption for N consecutive times, calculating a display value XN according to a second formula: $X_N=(VO_2max1+VO_2max2 \ldots VO_2maxN)/N$, wherein $N \geq 1$, $VO_2maxN$ indicates the maximal oxygen consumption calculated at the Nth time.

Preferably, wherein the one or more processors are further configured to calculate a moving average Xy of subsequent maximal oxygen consumptions by using a moving average algorithm with a fixed calculation length M and update the current display value with the moving average Xy.

The present invention also discloses a readable storage medium in which programs are stored, and the programs are executed by the processor, to implement a method for dynamically acquiring maximal oxygen consumption, the method includes acquiring a user's age, gender, weight, resting heart rate and maximum heart rate, detecting basic heart rate data including a plurality of exercise heart rates and basic speed data including a plurality of exercise speeds, calculating a characteristic heart rate and a characteristic speed based on the basic heart rate data and the basic speed data, and calculating the user's maximal oxygen consumption according to the user's age, gender, weight, resting heart rate and maximum heart rate, the characteristic heart rate and the characteristic speed.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

In order to explain in detail the technical content, construction features, the purpose and effect achieved by the present invention, the following combined with the implementation and the attached drawings are described in detail.

Figure 1:
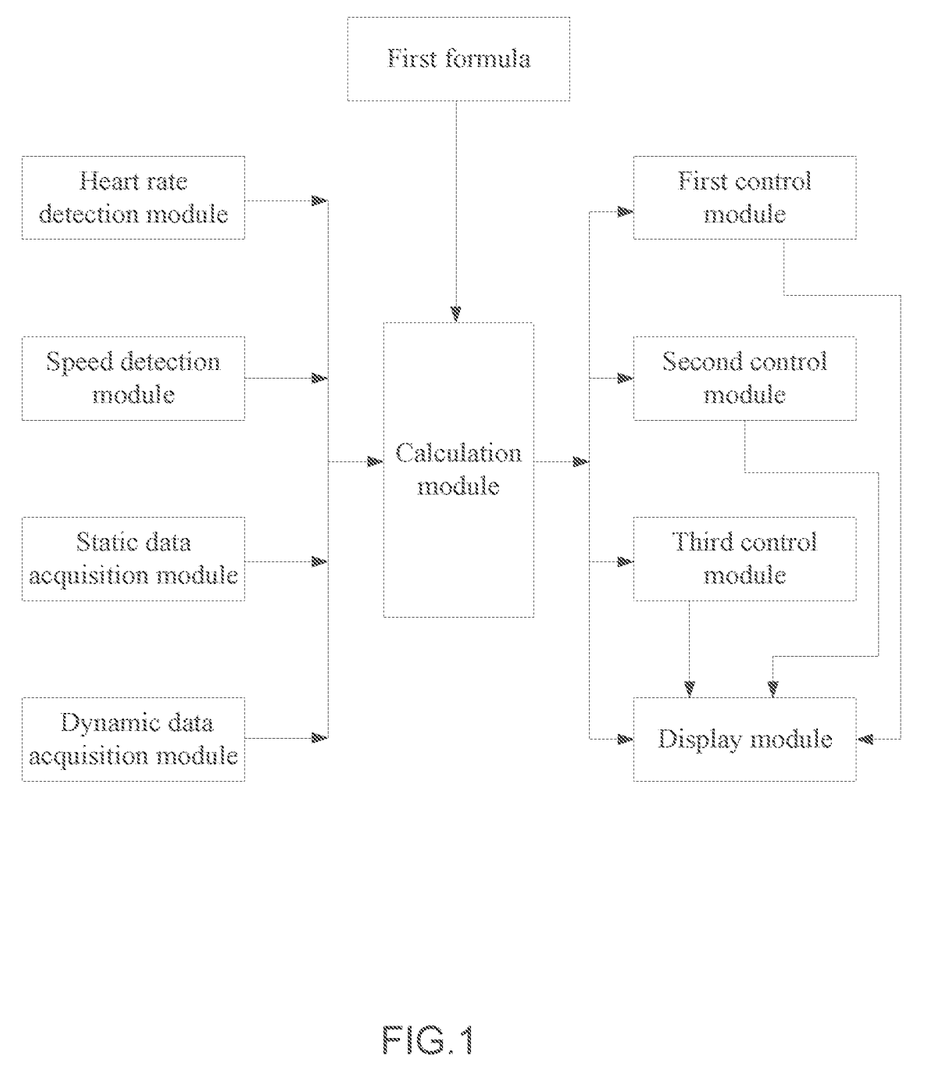
FIG. 1 is a schematic diagram of an electronic device for dynamically acquiring maximal oxygen consumption according to an embodiment of the present invention.

As shown in FIG. 1, the present invention discloses an electronic device for dynamically acquiring maximal oxygen consumption, which includes a portable base (such as a sports electronic watch) on which a heart rate detection module, a speed detection module, a static data acquisition module, a dynamic data acquisition module and a calculation module are configured.

The heart rate detection module is configured to detect a user's real-time heart rate, and the speed detection module is configured to detect a real-time exercise speed of the user's body movement. In this embodiment, the heart rate detection module includes a heart rate sensor installed on the base, and the speed detection module includes a GPS system installed on the base.

The static data acquisition module is configured to acquire static data such as the user's age, gender, weight, resting heart rate, and maximum heart rate. The resting heart rate is the heart rate value of a user under awake and quiet state, the maximum heart rate can be preset or generated in real time according to the user's age characteristics. In this embodiment, the maximum heart rate is preferably obtained by calculation, through the formula $HR_{max}=208-0.7*a$, where $HR_{max}$ denotes the maximum heart rate, and a is the age value input by the user. Data such as a user's age and gender can be input through common input systems such as screen input, key input or voice input. In addition, resting heart rate and maximum heart rate can also be input through input system, and can also be detected by a heart rate sensor set on the base.

The dynamic data acquisition module is configured to acquire dynamic data such as basic heart rate data during exercise and basic speed data reflecting body movement speed.

The calculation module is configured to calculate maximal oxygen consumption by selecting time window data.

Specifically, the method for dynamically acquiring maximal oxygen consumption by the above electronic device is described below.

Figure 2:
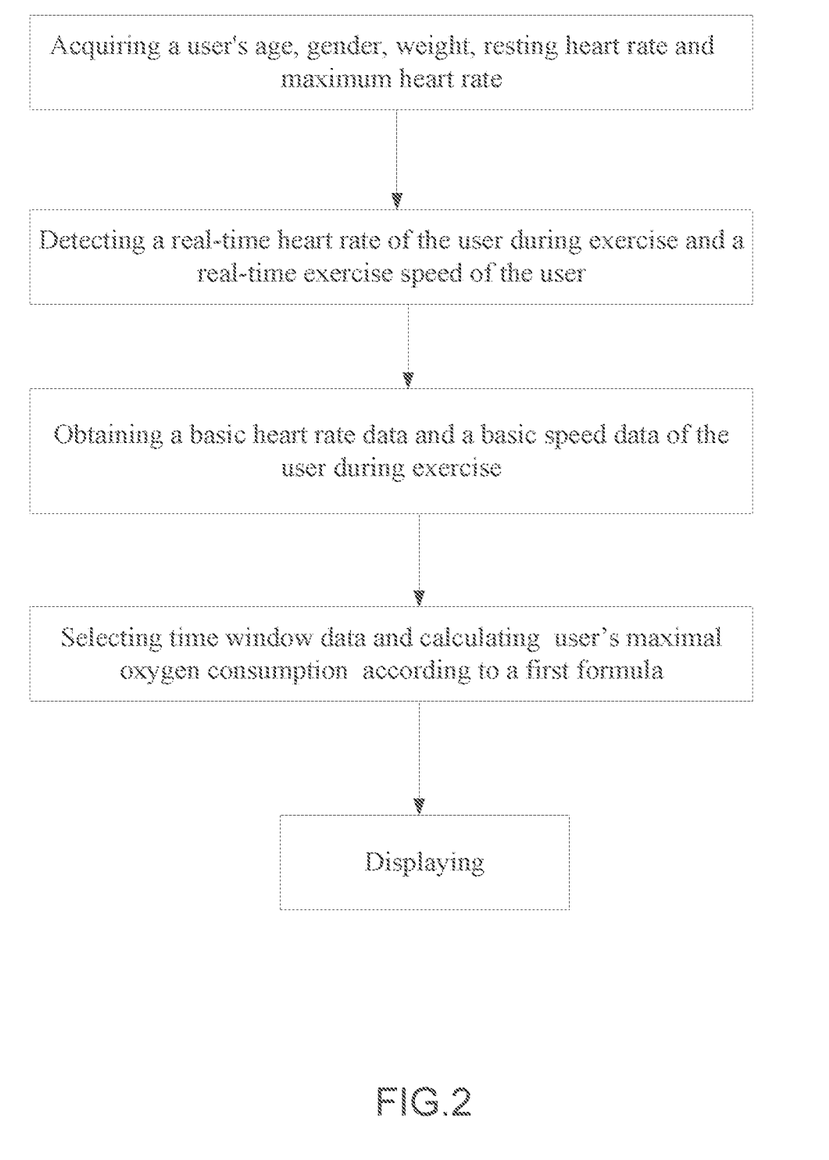
FIG. 2 is a flowchart of the electronic device according to an embodiment of the present invention.

As shown in FIG. 2, first, data such as a user's age, gender, weight are obtained through an input system, and then the maximum heart rate is obtained through calculation or input system, and the resting heart rate is obtained through detection or input system. Then, the user's real-time heart rate and real-time exercise speed are obtained by the heart rate sensor and the GPS system set on the base, so as to obtain the users basic heart rate data and basic speed data during exercise. When the user exercises for a certain period of time, the calculation module selects time window data, that is, selects a characteristic time period with a preset time length from the user's exercise period, and uses an arithmetic average algorithm to calculate a characteristic average heart rate and a characteristic average speed in the characteristic time period based on the basic heart rate data and basic speed, and finally calculate the current user's maximal oxygen consumption $V_{O_2max}$ according to the following first formula:

$$VO_2max = A + P1*S - P2*G + P3*V*\frac{P4}{B} - C*\frac{HR_{chara} - HR_{rest}}{HR_{max} - HR_{rest}} - \frac{2(a-26)}{5},$$

wherein A is a constant from 40 to 50, P1 is a constant from 7 to 8, S is a gender constant, male is equal to 1, and female is equal to 0; P2 is a constant from 0.1 to 0.2, G is the user's weight; P3 is a constant from 4 to 5, V is characteristic average speed, P4 is a constant from 3 to 4, B is a constant from 1 to 2; C is a constant from 15 to 20, $HR_{chara}$ is characteristic average heart rate, $HR_{rest}$ is resting heart rate in a quiet state for the user, $HR_{max}$ is maximum heart rate; and a is user's age.

Figure 3:
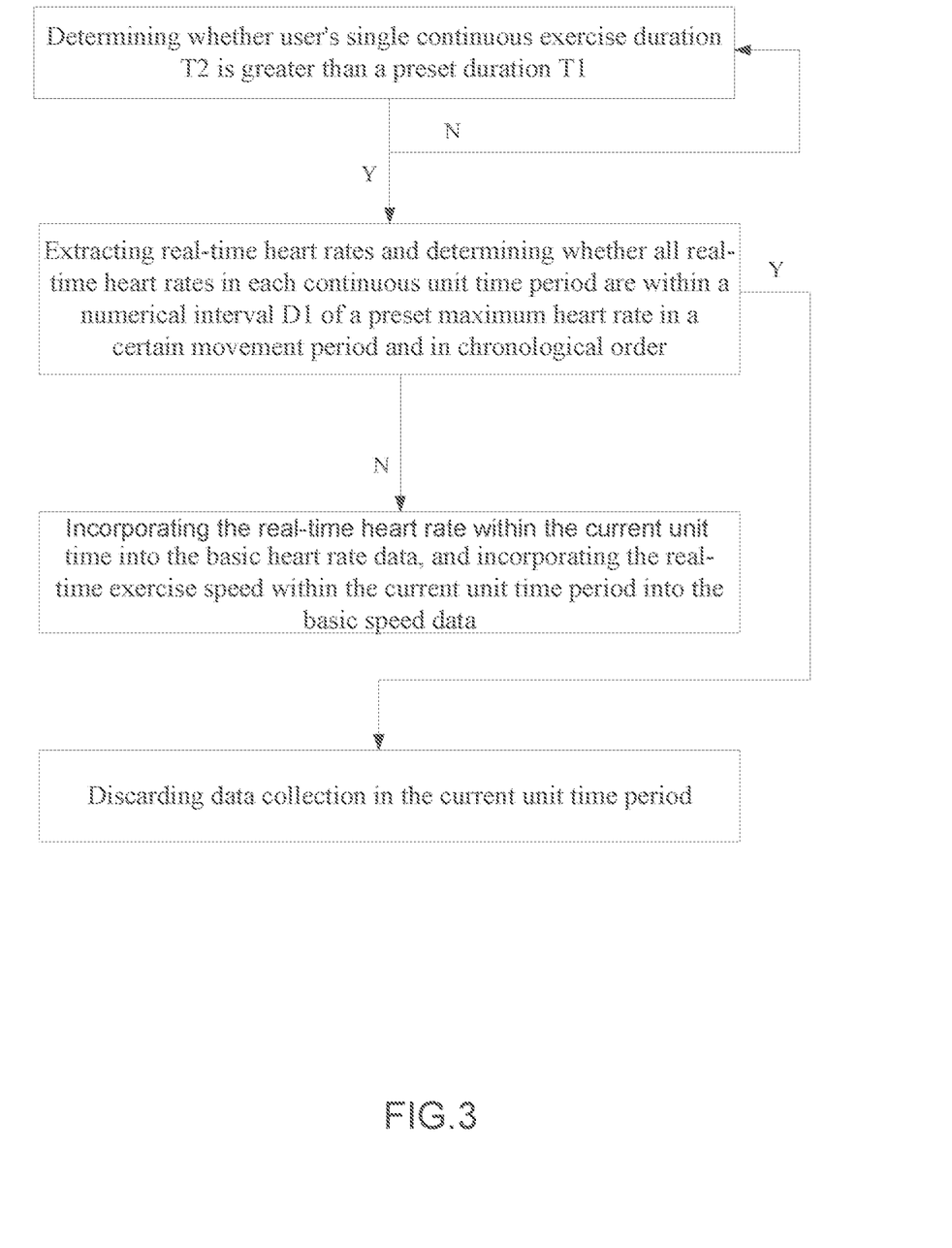
FIG. 3 is a flowchart of a screening process for obtaining basic heart rate data and basic speed data according to an embodiment of the present invention.

In the above embodiment, in order to make the maximal oxygen consumption calculated by the electronic device close to the actual data to the greatest extent, referring to FIG. 3, the basic heart rate data and basic speed data can be obtained through a method of condition screening, which specifically includes the following steps:

S1, determining whether user's single continuous exercise duration T2 is greater than a preset duration T1, if yes, performing step S2; otherwise, return;

S2, extracting real-time heart rates in each continuous unit time period and determining whether all real-time heart rates in each continuous unit time period are within a numerical interval D1 of a preset maximum heart rate in a certain movement period and in chronological order, if yes, incorporating the real-time heart rate within the current unit time into the basic heart rate data, and incorporating the real-time exercise speed within the current unit time period into the basic speed data, otherwise, the current collected data is discarded. In this embodiment, the numerical interval D1 is 70% *$HR_{max}$<D1<95% * $HR_{max}$, preferably.

Specifically, if the exercise duration T2 of the user is greater than T1, taking a unit time period of one minute as an example, if the movement period is one second, in chronological order, all real-time heart rate data in one-minute time period such as 1st second-60th second, 2nd second-61st second, 3rd second-62nd second, . . . etc. are respectively detected mid judged to be within the numerical range D1 or not, if so, incorporating the real-time heart rate data in this one-minute time period into the basic heart rate data, meanwhile incorporating the real-time exercise speed in this one-minute time period into the basic speed data.

Furthermore, the characteristic average heart rate and the characteristic average speed are calculated by following steps:

selecting a characteristic time period with a preset time length from the user's exercise time period;

respectively performing an averaging operation to the basic heart rate data in each unit time period selected in the characteristic time period to obtain a plurality of unit average heart rates;

respectively performing an averaging operation to the basic speed data in each unit time period selected in the characteristic time period to obtain a plurality of unit average speeds;

performing an average operation to the plurality of unit average heart rates to obtain the characteristic average heart rate; and performing an averaging operation to the plurality of unit average speeds to obtain the characteristic average speed.

For the selection of the time window (characteristic time period), preferably, when the preset duration T1 is greater than or equal to 10 minutes, when the user's continuous exercise duration T2 is greater than 30 minutes, the characteristic time period is a period of exercise time between 10 to 30 minutes; and when the user's continuous exercise duration T2 is less than or equal to 30 minutes, the characteristic time period is a period of exercise time between 10 to T2.

The method of dynamic dynamically acquiring maximal oxygen consumption by the electronic device in the above embodiment is described in detail as follow.

The threshold of the duration T1 of the user's single continuous exercise duration is set to 20 minutes. Before the user starts exercising, the electronic device is operated, and corresponding data such as age, gender, weight, resting heart rate, etc. are input to the electronic device. During exercise, the electronic device detects and records the user's real-time heart rate and real-time exercise speed, and obtains basic heart rate data and basic speed data through the above-mentioned condition screening method. When the user exercises for 30 minutes, if a command to output the maximal oxygen consumption is sent to the electronic device (which can be realized by key pressing), basic heart rate data and basic speed data in each one minute filtered out in the time window (10th to 30th minute) can be found our, and unit average heart rate HR1 and unit average speed V1 in each one minute can be calculated by using an arithmetic average algorithm. Then, in the same way, using the arithmetic average algorithm, the characteristic average heart rate $HR_{chara}$ and the characteristic average speed V within the time window can be calculated based on basic data including HR1 and V1. Finally, maximal oxygen consumption can be obtained by substituting the characteristic average heart rate $HR_{chara}$ and the characteristic average speed V into the first formula.

Further, the electronic device is also provided with a display module to display the maximal oxygen consumption and a display control module. Preferably, in order to make the displayed maximal oxygen consumption have a gradual change trend, the display control module includes a first control module. When the maximal oxygen consumption is calculated for N consecutive times, the first control module is configured to calculate the display value $X_N$ of the display module by using the second formula: $X_N=(VO_2max1+VO_2max2 \ldots VO_2maxN)/N$, wherein $N \geq 1$, $VO_2maxN$ indicates the maximal oxygen consumption calculated at the Nth time. For example, if a first maximal oxygen consumption $V_{o_2max}$ is calculated, the display value $X_N=VO_2max1$; if a second maximal oxygen consumption $V_{o_2max2}$ is calculated, the display value $X_N=(VO_2max1+VO_2max2)/2$; if a third maximal oxygen consumption $VO_2max3$ is calculated, the display value $X_N=(VO_2max1+VO_2max2+VO_2max3)/3$, . . . and soon.

Preferably, the display control module further includes a second control module. If the second control module detects that the current calculation limes N of the maximal oxygen consumption exceeds the preset value M, continuously calculating a moving average $X_y$ of subsequent maximal oxygen consumptions by using a moving average algorithm with a fixed calculation length M, and determining whether the moving average $X_y$ is greater than a current display value, if yes, updating the current display value with the moving average $X_y$. If the second control module detects that the current calculation times N of the maximal oxygen consumption does not exceed the preset value M, calculating the display value according to the second formula. Specifically, if M is set to 5, the maximal oxygen consumptions at the previous 5 times are all calculated by the above-mentioned second formula and then displayed as the respective display value. To the sixth time, the average value $X_y$ of the most recent five maximal oxygen consumptions (that is, $VO_2max2$, $VO_2max3$, $VO_2max4$, $VO_2max5$, $VO_2max6$) is calculated and then judged if the value $X_y$ is larger than the current display value (that is the average value of the previous five maximal oxygen consumptions) or not, if yes, update the current display value with $X_y$; otherwise, maintain the current display value.

Preferably, the display control module further includes a third control module. When the third control module detects that the maximal oxygen consumption for M consecutive times is smaller than the current display value, the display value is updated with the average value of the maximal oxygen consumptions. Still taking M equal to 5 as an example, when each of the maximal oxygen consumption for the five consecutive times is smaller than the current display value, the current display value is updated with the average value of the current five maximal oxygen consumptions. In such a way, user's own aerobic capacity level can be accurately judged and any decreases on the aerobic capacity level can be captured timely.

In addition, when the electronic device takes no operation of calculating maximal oxygen consumption for a long time, such as more than 60 days, the data will be re-recorded and refreshed once an operation of calculating maximal oxygen consumption is restarted, meanwhile the static data will also be re-collected.

Additionally, the present invention discloses an electronic system for dynamically acquiring maximal oxygen consumption, including one or more processors; one or more memories; and one or more programs, stored in said one or more memories and configured to be executed by said one or more processors, for executing the method for dynamically acquiring maximal oxygen consumption mentioned above.

The present invention also discloses a computer readable storage medium in which programs are stored. When the programs are executed by the processor, to implement the method for dynamically acquiring maximal oxygen consumption as described above.

In comparison with the prior art, the method for dynamically acquiring maximal oxygen consumption of the present invention not only needs to collect static data such as the user's age, gender, weight, resting heart rate, and maximum heart rate, but also needs to collect dynamic data such as the user's current basic heart rate data during exercise and basic speed data of body movement, and the basic heart rate data and basic speed data in the characteristic time period selected from the user's current exercise time are processed by an average algorithm to obtain the characteristic heart rate mid characteristic speed. Then, data such as age, gender, weight, resting heart rate, maximum heart rate, characteristic average heart rate, and characteristic average speed are substituted into a formula to obtain the user's maximal oxygen consumption during the current exercise. By this token, on one hand, the maximal oxygen consumption during each exercise can be dynamically calculated, thereby providing accurate reference data for the user to evaluate the current aerobic capacity level; on the other hand, by using the formula to calculate the maximal oxygen consumption in the present invention, both static data and dynamic data of the user are combined, to achieve a high-accurate detection result. In addition, through the combination of the display control module and the display module, a trend change of the maximal oxygen consumption may be shown, by which the users can adjust the weight coefficient of training load.

While the invention has been described in connection with what are presently considered to be the most practical and preferred embodiments, it is to be understood that the invention is not to be limited to the disclosed embodiments, but on the contrary, is intended to cover various modifications and equivalent arrangement included within the spirit and scope of the invention.

What is claimed is:

1. A computer-implemented method for dynamically acquiring maximal oxygen consumption (VO$_2$max), comprising:
    acquiring a user's age, gender, weight, resting heart rate and maximum heart rate;
    detecting basic heart rate data through a heart rate sensor installed on a base carried by the user, the basic heart rate data comprising a plurality of exercise heart rates;
    detecting basic speed data through a GPS system installed on the base, the basic speed data comprising a plurality of real-time exercise speeds, wherein the basic speed data is obtained by detecting the plurality of real-time exercise speeds through the GPS system and calculating based on the plurality of real-time exercise speeds through a method of condition screening;
    calculating a characteristic average heart rate and a characteristic average speed based on the basic heart rate data and the basic speed data; and
    calculating the user's maximal oxygen consumption according to the user's age, gender, weight, resting heart rate and maximum heart rate, the characteristic average heart rate and the characteristic average speed;
    wherein the user's maximal oxygen consumption is calculated according to a first formula:

$$VO_2\text{max} = A + P1*S - P2*G + P3*V * \frac{P4}{B} - C * \frac{HR_{chara} - HR_{rest}}{HR_{max} - HR_{rest}} - \frac{2(a-26)}{5},$$

wherein A is a constant from 40 to 50, P1 is a constant from 7 to 8, S is a gender constant, male is equal to 1, and female is equal to 0; P2 is a constant from 0.1 to 0.2, G is user's weight; P3 is a constant from 4 to 5, V is characteristic average speed, P4 is a constant from 3 to 4, B is a constant from 1 to 2; C is a constant from 15 to 20, $HR_{chara}$ is characteristic average heart rate, $HR_{rest}$ is resting heart rate in a quiet state for user, $HR_{max}$ is maximum heart rate; and a is user's age.

2. The computer-implemented method for dynamically acquiring maximal oxygen consumption as claimed in claim 1, wherein the characteristic average heart rate is calculated by averaging the basic heart rate data and the characteristic average speed is calculated by averaging the basic speed data.

3. The computer-implemented method for dynamically acquiring maximal oxygen consumption as claimed in claim 1, wherein calculating the characteristic average heart rate and the characteristic average speed based on the basic heart rate data and the basic speed data comprises:
    detecting first basic heart rate data and second basic heart rate data;
    detecting first basic speed data and second basic speed data;
    generating a first unit heart rate and a second unit heart rate by averaging the first basic heart rate data and the second basic heart rate data respectively;
    generating a first unit speed and a second unit speed by averaging the first basic speed data and the second basic speed data respectively;
    calculating the characteristic average heart rate by averaging the first unit heart rate and the second unit heart rate; and
    calculating the characteristic average speed by averaging the first unit speed and the second unit speed.

4. The computer-implemented method for dynamically acquiring maximal oxygen consumption as claimed in claim 1, wherein when the maximum heart rate is generated in real time according to the user's age, the maximum heart rate is calculated by following formula: $HR_{max}=208-0.7*a$.

5. The computer-implemented method for dynamically acquiring maximal oxygen consumption as claimed in claim 1, wherein the basic heart rate data and the basic speed data are detected when the user's single continuous exercise exceeds a preset duration.

6. The computer-implemented method for dynamically acquiring maximal oxygen consumption as claimed in claim 1, further comprising displaying a calculated maximal oxygen consumption by following steps:
    when calculating the maximal oxygen consumption for N consecutive times, calculating a display value $X_N$ according to a second formula: $X_N=(VO_2\text{max}1+VO_2\text{max}2 \ldots VO_2\text{max}N)/N$, wherein $N≥1$, $VO_2\text{max}N$ indicates the maximal oxygen consumption calculated at the Nth time.

7. The computer-implemented method for dynamically acquiring maximal oxygen consumption as claimed in claim 6, further comprising:
    determining whether a current number of consecutive calculations of maximal oxygen consumption N exceeds a present value M, if not, calculating the display value according to the second formula; otherwise, continuously calculating a moving average $X_y$ of subsequent maximal oxygen consumptions by using a moving average algorithm with a fixed calculation length M, and determining whether the moving average $X_y$ is greater than a current display value, if yes, updating the current display value with the moving average $X_y$.

8. An electronic device for dynamically acquiring maximal oxygen consumption (VO$_2$max), comprising:
    a base configured to be carried by a user;
    a heart rate detection module comprising a heart rate sensor installed on the base and configured to detect basic heart rate data comprising a plurality of exercise heart rates;
    a speed detection module comprising a GPS system installed on the base and configured to detect basic speed data comprising a plurality of real-time exercise speeds, wherein the basic speed data is obtained by detecting the plurality of real-time exercise speeds through the GPS system and calculating based on the plurality of real-time exercise speeds through a method of condition screening; and
    one or more processors configured to:
        acquire the user's age, gender, weight, resting heart rate and maximum heart rate;
        calculate a characteristic average heart rate and a characteristic average speed based on the basic heart rate data and the basic speed data; and
        calculate the user's maximal oxygen consumption according to the user's age, gender, weight, resting heart rate and maximum heart rate, the characteristic average heart rate and the characteristic average speed;

wherein the one or more processors are further configured to calculate the user's maximal oxygen consumption according to a first formula:

$$VO_2\text{max} = A + P1*S - P2*G + P3*V*\frac{P4}{B} - C*\frac{HR_{chara} - HR_{rest}}{HR_{max} - HR_{rest}} - \frac{2(a-26)}{5},$$

wherein A is a constant from 40 to 50, P1 is a constant from 7 to 8, S is a gender constant, male is equal to 1, and female is equal to 0; P2 is a constant from 0.1 to 0.2, G is user's weight; P3 is a constant from 4 to 5, V is characteristic average speed, P4 is a constant from 3 to 4, B is a constant from 1 to 2; C is a constant from 15 to 20, $HR_{chara}$ is characteristic average heart rate, $HR_{rest}$ is resting heart rate in a quiet state for user, $HR_{max}$ is maximum heart rate; and a is user's age.

9. The electronic device for dynamically acquiring maximal oxygen consumption as claimed in claim 8, wherein to calculate the characteristic average heart rate and the characteristic average speed, the one or more processors are further configured to:
calculate the characteristic average heart rate by averaging the basic heart rate data; and
calculate the characteristic average speed by averaging the basic speed data.

10. The electronic device for dynamically acquiring maximal oxygen consumption as claimed in claim 8, wherein to calculate the characteristic average heart rate and the characteristic average speed, the one or more processors are further configured to:
detect first basic heart rate data and second basic heart rate data;
detect first basic speed data and second basic speed data;
generate a first unit heart rate and a second unit heart rate by averaging the first basic heart rate data and the second basic heart rate data respectively;
generate a first unit speed and a second unit speed by averaging the first basic speed data and the second basic speed data respectively;
calculate the characteristic average heart rate by averaging the first unit heart rate and the second unit heart rate; and
calculate the characteristic average speed by averaging the first unit speed and the second unit speed.

11. The electronic device for dynamically acquiring maximal oxygen consumption as claimed in claim 9, wherein when the maximum heart rate is generated in real time according to the user's age, the maximum heart rate is calculated by following formula: $HR_{max}=208-0.7*a$.

12. The electronic device for dynamically acquiring maximal oxygen consumption as claimed in claim 8, wherein the basic heart rate data and the basic speed data are detected when the user's single continuous exercise exceeds a preset duration.

13. The electronic device for dynamically acquiring maximal oxygen consumption as claimed in claim 8, wherein the one or more processors are further configured to calculate a display value based on following steps:
when calculating the maximal oxygen consumption for N consecutive times, calculating the display value XN according to a second formula: $X_N=(VO_2\text{max1}+VO_2\text{max2}....VO_2\text{maxN})/N$, wherein N≥1, $VO_2\text{maxN}$ indicates the maximal oxygen consumption calculated at the Nth time.

14. The electronic device for dynamically acquiring maximal oxygen consumption as claimed in claim 13, wherein the one or more processors are further configured to:
calculate a moving average Xy of subsequent maximal oxygen consumptions by using a moving average algorithm with a fixed calculation length M; and
update a current display value with the moving average Xy.

15. A non-transitory computer readable storage medium, comprising computer programs configured to be executed by a processor to perform a computer-implemented method for dynamically acquiring maximal oxygen consumption ($VO_2$max), the computer-implemented method comprising:
acquiring a user's age, gender, weight, resting heart rate and maximum heart rate;
detecting basic heart rate data through a heart rate sensor installed on a base carried by the user, the basic heart rate data comprising a plurality of exercise heart rates;
detecting basic speed data through a GPS system installed on the base, the basic speed data comprising a plurality of real-time exercise speeds, wherein the basic speed data is obtained by detecting the plurality of real-time exercise speeds through the GPS system and calculating based on the plurality of real-time exercise speeds through a method of condition screening;
calculating a characteristic average heart rate and a characteristic average speed based on the basic heart rate data and the basic speed data; and
calculating the user's maximal oxygen consumption according to the user's age, gender, weight, resting heart rate and maximum heart rate, the characteristic average heart rate and the characteristic average speed;
wherein the user's maximal oxygen consumption is calculated according to a first formula:

$$VO_2\text{max} = A + P1*S - P2*G + P3*V*\frac{P4}{B} - C*\frac{HR_{chara} - HR_{rest}}{HR_{max} - HR_{rest}} - \frac{2(a-26)}{5},$$

wherein A is a constant from 40 to 50, P1 is a constant from 7 to 8, S is a gender constant, male is equal to 1, and female is equal to 0; P2 is a constant from 0.1 to 0.2, G is user's weight; P3 is a constant from 4 to 5, V is characteristic average speed, P4 is a constant from 3 to 4, B is a constant from 1 to 2; C is a constant from 15 to 20, $HR_{chara}$ is characteristic average heart rate, $HR_{rest}$ is resting heart rate in a quiet state for user, $HR_{max}$ is maximum heart rate; and a is user's age.

16. The non-transitory computer readable storage medium as claimed in claim 15, wherein the characteristic average heart rate is calculated by averaging the basic heart rate data and the characteristic average speed is calculated by averaging the basic speed data.

* * * * *